US006204064B1

(12) United States Patent
Alberts et al.

(10) Patent No.: US 6,204,064 B1
(45) Date of Patent: Mar. 20, 2001

(54) MEASUREMENT OF LESION PROGRESSION VIA MAPPING OF CHROMATIN TEXTURE FEATURES ALONG PROGRESSION CURVE

(76) Inventors: David S. Alberts, 250 N. Indian House Rd., Tucson, AZ (US) 85711; Peter H. Bartels, 10625 E. Speedway Blvd., Tucson, AZ (US) 85748

( * ) Notice: Subject to any disclaimer, the term of this patent is extended or adjusted under 35 U.S.C. 154(b) by 0 days.

(21) Appl. No.: 09/239,226

(22) Filed: Jan. 30, 1999

(51) Int. Cl.[7] .................................................. G01N 33/48
(52) U.S. Cl. ............................ 436/63; 436/64; 436/164; 436/174; 382/128; 382/133
(58) Field of Search .............................. 436/63, 64, 164, 436/174, 813; 435/1, 4, 6, 29, 40.52; 702/19, 21; 382/128, 133

(56) References Cited

U.S. PATENT DOCUMENTS 5,146,923 * 9/1992 Dhawan ................................ 600/476
6,025,128 * 5/2000 Veltri et al. ............................. 435/6

OTHER PUBLICATIONS

Bartels et al. *Analytical and Quantitative Cytology and Histology*, vol. 20, No. 5, pp. 389–396, Oct. 1998.*
Bartels et al. *Analytical and Quantitative Cytology and Histology*, vol. 20, No. 5, pp. 381–388, Oct. 1998.*
Christen et al. *Analytical and Quantitative Cytology and Histology*, vol. 15, No. 6, pp. 383–388, 1993.*
Bartels et al. *Analytical and Quantitative Cytology and Histology*, vol. 20, No. 5, pp. 407–416, Oct. 1998.*
Bibbo et al. *Analytical and Quantitative Cytology and Histology*, vol. 13, No. 1, pp. 61–68, Feb. 1991.*
Bacus, James W., Bacus, James V., Stoner, Gary D., Moon, Richard C., Kelloff, Gary J., Boone, Charles W., "Quantitation of Preinvasive Neoplastic Progression Animal Models of Chemical Carcinogenesis", *Journal of Cellular Biochemistry Supplements*, 28/29:21–38 (1997).

Bostwick, David G., Brawer, Michael K., "Prostatic Intra–Epithelial Neoplasia and Early Invasion in Prostate Cancer", *Cancer*, Feb. 15, 1987, vol. 59, No. 4, 788–794.
Bozzo, Paul D., Vaught, Linda C., Alberts, David S., Thompson, Deborah, Bartels, Peter H., "Nuclear Morphometry in Solar Keratosis", *Analytical and Quantitative Cytology and Histology*, vol. 20, No. 1, Feb. 1998, pp. 21–28.
Bacus, Sarah, Chin, Dot, Stewart, James, Zelnick, Carolyn, Mahvi, David, Gilchrist, Kennedy, "Potential Use of Image Analysis for the Evaluation of Cellular Predicting Factors for Therapeutic Response in Breast Cancers", *Analytical and Quantitative Cytology and Histology*, vol. 19, No. 4, Aug. 1997, pp. 316–328.
Boone, Charles W., Bacus, James W., Bacus, James V., Steele, Vernon E., Kelloff, Gary J., "Properites of Intraepithelial Neoplasia Relevant to the Development of Cancer Chemopreventive Agents", *Journal of Cellular Biochemistry Supplements*, 28/29:1–20 (1997).
Boone, Charles W., Bacus, James W., Bacus, James V., Steele, Vernon E., Kelloff, Gary J., "Properties of Intraepithelial Neoplasia Relevant to Cancer Chemoprevention and to the Development of Surrogate End Points of Clinical Trials", *P.S.E.B.M.*, 1997, vol. 216, pp. 151–165.

* cited by examiner

Primary Examiner—Maureen M. Wallenhorst
(74) Attorney, Agent, or Firm—Cahill, Sutton & Thomas P.L.C.

(57) ABSTRACT

A method is disclosed for quantitatively measuring the progression of a lesion toward malignant disease by digitizing images of clinical samples of biopsied lesions using a microphotometer that includes a video camera, and a computer that includes a video frame capture board. The digitized image is analyzed to locate the borders of cell nuclei within the captured video image, and one or more chromatin texture features within such nuclei are processed by the computer to arrive at a numerical value. This numerical value is compared to a monotonic progression curve that has been previously established by using the same procedure on known clinical samples ranging from normal tissue to malignant disease. The method can also be used to test the efficacy of chemopreventive drugs and treatments.

24 Claims, 4 Drawing Sheets

MEASUREMENT OF LESION PROGRESSION VIA MAPPING OF CHROMATIN TEXTURE FEATURES ALONG PROGRESSION CURVE

STATEMENT REGARDING FEDERALLY SPONSORED RESEARCH

This invention was made with government support under Contract No. NIH CA53877 awarded by the National Institutes of Health (NIH) to the University of Arizona. The U.S. Government has a paid-up license in this invention.

BACKGROUND OF THE INVENTION

1. Field of the Invention

The present invention relates generally to methods for analyzing biological samples, and more particularly, to the assessment of clinical biological sectioned samples using computerized digitizing techniques.

2. Description of the Relevant Art

The incidence of non-melanoma skin cancers is increasing dramatically throughout the United States. The vast majority of these cancers develop in areas of severe sun damage, particularly within or contiguous to areas of solar keratoses, but it has not been possible thus far to predict who will develop these potentially dangerous skin cancers. Although the mortality rate for these skin cancers is low, their treatment is associated with considerable morbidity and significant medical care costs.

Efforts to characterize the histopathological and karyometric changes induced by solar keratosis face difficulties in defining a standard. First, there is the variety of skin types. At best, "skin type" constitutes a fuzzy categorization. There is the difficulty of defining exposure, its nature and total duration for a given individual; this source of variation requires that comparisons be made between a visually apparent region of solar keratosis and an adjacent, seemingly unaffected skin area. Such an area, in all likelihood, would have received a comparable dose of solar irradiation. Well-defined samples of entirely unexposed skin, desirable for comparison with the changes induced by solar radiation, are usually not available. One option is a comparison to skin biopsies taken from remote, minimally exposed body sites. At this time there exists no database that characterizes the nuclear chromatin features of skin samples of such an origin.

Similar problems arise in attempts to define the efficacy of chemopreventive treatment of solar keratosis lesions. One cannot take a second biopsy from the original lesion since epidermal change and dermal fibrosis may introduce additional variability. If a different solar keratosis lesion is biopsied to assess treatment efficacy, one may bias the sampling because the selected site constitutes a lesion that most likely persisted throughout treatment.

The same general problems arise when attempting to detect and analyze other types of lesions in tissues other than the skin, e.g., breast lesions, prostatic lesions, endometrial legions, esophogeal lesions, etc. Currently known methods of analyzing clinical samples of such tissues tend to be qualitative in nature, and are often subjective rather than objective. Moreover, currently known methods of analyzing such clinical samples do not detect changes in the nature of such lesions except after relatively long periods of time. Evaluation of premalignant lesions is typically made by a visual assessment and is expressed in terms of categories of lesions, such as "hyperplasia", or "severe adenoma", or as a grade, such as grade II or grade IV, or as "low grade" and "high grade". Such linguistic labels are vague and difficult to reproduce consistently between observers, or even by the same observer. As measures to assess the efficacy of a chemopreventive agent, they lack precision and the ability to detect a small, but significant change. Nevertheless, the existing diagnostic terms, fuzzy and vague as they are, do represent the current state of knowledge and ultimately the standard from which the clinical effect of treatment by chemopreventive agents has been assessed.

The study of sectioned images of lesions is generally known. For example, in the technical article by Bostwick and Brawer entitled "Prostatic Intra-Epithelial Neoplasia and Early Invasion in Prostate Cancer", *Cancer* 59:788–794, 1987, the authors describe the process of marking prostatic basal cell layers using a monoclonal antibody to certain keratin proteins. Disruption of the basal layer was used to detect early invasion in prostate cancer. Among the characteristics studied by Bostwick and Brawer were crowding and multilayering of cells, variation in nuclear size and the prominence of nucleoli. In most instances, subjective inspection of the histological appearance of sectioned and stained material is carried out by experienced pathologists, but despite the experience of such individuals, the process remains subjective and qualitative.

In the paper by Bacus, Bacus, Stoner, Moon, Kelloff, and Boone entitled "Quantitation of preinvasive neoplastic progression in animal models of chemical carcinogenesis", *J Cell Biochem Suppl,* 1997; 28–29:21–38, the authors describe the use of image analysis through the use of high-resolution tiled images of complete tissue sections to quantitate cellular and tissue changes associated with early, preinvasive neoplasia. The image analysis was applied to histological sections of tissue that had been sectioned and stained. The authors describe a histological grading system, or scale, expressed in normal deviate units of multiple and different morphometric descriptors. However, those skilled in the art have as yet failed to provide a method of quantitatively expressing how far a tissue has progressed from normal to malignant disease. Likewise, those skilled in the art have not provided a method for reliably detecting changes in the status of tissue under study in a relatively prompt manner. If reliable detection and quantitative assessment of such changes could be performed relatively quickly, then the efficacy of chemopreventive drugs or treatments could be evaluated much more quickly, and promising drugs and/or treatments could be brought into use in shorter periods of time.

Accordingly, it is an object of the present invention to provide a method for quantitatively measuring the progression of a lesion along a progression curve ranging between normal tissue and malignant disease.

A further object of the present invention is to provide a method of objectively assessing and grading sampled tissue to assign a progression index value to a lesion.

A still further object of the present invention is to quantitatively detect and assess changes in tissue over a relatively short period of time.

Yet another object of the present invention is to rapidly and quantitatively determine the efficacy of a chemopreventive drug or treatment in combating progression of tissue from its normal state toward malignant disease.

These and other objects of the present invention will become more apparent to those skilled in the art as the present description proceeds.

SUMMARY OF THE INVENTION

Briefly described, and in accordance with a preferred embodiment thereof, the present invention relates to a method for quantitatively measuring the progression of a lesion, wherein the method includes the initial step of preparing a clinical sampled section of a biopsied lesion. The sampled section is then magnified, and a video image is formed of the magnified sampled section with a video camera, e.g., by using a microphotometer. The video image is then digitized and stored electronically, e.g., in computer storage. The stored digitized image is then analyzed to locate the boundaries of cell nuclei within the cells captured by the digitized video image. Once the boundaries of such cell nuclei are recognized, one or more chromatin texture features, or "chromatin signatures", of the cell nuclei image are computed or processed by the computer, effectively converting the two-dimensional digitized image of the nuclei into a single numerical value. By way of example, one such chromatin texture feature that can be used is the total optical density, or "brightness", of the measured nuclei images.

The computed numerical value of the chromatin texture feature(s) obtained from the steps mentioned above is then compared to a progression curve previously established by subjecting known clinical samples to the same steps. For example, known clinical samples of tissue ranging between normal tissue to tissue exhibiting malignant disease are subjected to the same steps to produce a corresponding range of index values. These index values are used to plot a progression curve showing the progression of a lesion from normal tissue all the way to malignant disease. Preferably, the chromatin texture feature(s) selected to measure the nuclei exhibit a monotonically increasing or decreasing relationship to the degree of progression of the lesion from normal tissue to malignant disease. Likewise, the selected chromatin texture feature(s) should exhibit a statistically significant change as between the extremes of normal tissue and malignant disease.

Having established such a progression curve, the particular unknown sectioned sample under study can be quickly and quantitatively analyzed to provide a computed numerical value, as described above. This numerical value is then plotted upon the aforementioned progression curve to indicate how far the tissue has progressed from normal tissue toward malignant disease.

The aforementioned method can be used in conjunction with the same patient at two different times to measure the degree of change of a lesion over such period of time. The use of the method in this manner can be used to rapidly measure the efficacy of chemopreventive drugs or treatments in combating such malignant disease. Movement of the computed numerical value of the computed chromatin texture feature(s) along the progression curve during such predetermined time indicates the efficacy of a method for treating such lesion, i.e., whether, and by how much, such drugs or other treatment is causing such lesion to regress away from malignant disease.

The above-described method can be used to analyze lesions from a variety of different areas of the human body, including without limitation skin tissue lesions, prostatic lesions, breast tissue lesions, endometrial tissue lesions, and esophogeal tissue.

As mentioned above, the method described above can be used to quantitatively measure the efficacy of chemopreventive agents and/or treatments. The same basic steps are performed both before and after the administration of the chemopreventive agent or treatment to determine whether, and how much, the biopsied tissue has regressed away from malignant disease, and hence, the effectiveness of the chemopreventive agent.

DETAILED DESCRIPTION OF THE PREFERRED EMBODIMENT

Figure 1:
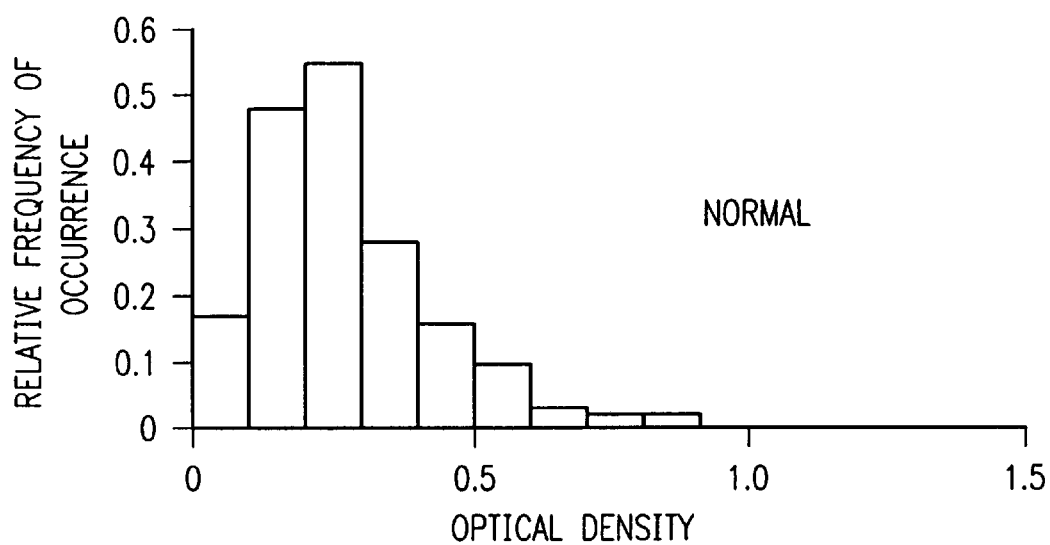
FIGS. 1 and 2 are graphs showing the relative frequency of occurrence of particular optical densities of nuclei sampled from normal tissue and from solar keratosis lesions, respectively.

The instrumentation required for the procedure is standard and consists of a microphotometer and a computer. The preferred microphotometer consists of a microscope equipped with a high numerical aperture, high resolution microscope objective and a videocamera. In the preferred embodiment, the microphotometer, or video-photometer, is equipped with a Zeiss (Oberkochen, Germany) planapochromatic oil immersion objective 63:1, N.A. 1.40, and a Cohu (San Diego, Calif.) black and white video camera; the image projected onto the face plate of the video camera, or vidicon, provides a sampling density of six pixels per micron. The microscope should have a well-regulated light source to guarantee reproducible photometry.

The clinical samples to be evaluated are typically biopsy material, presented as histopathologic sections. For example, when skin tissue samples are under study, a 4 mm. skin shave biopsy sample is fixed in ethanol and then sectioned to a 5 micron thickness and stained with H&E (hematoxylin and eosin) to prepare a microscopic slide. The videomicroscope may include an interference filter with maximum bandpass at 610 nm. to enhance the contrast of the H&E stained sections. The microscopic image of the biopsied clinical sample is projected onto the video camera, and the electronic image produced by the video camera is digitized and transferred to a "frame grabber", or "video capture" board installed in the computer. It is then stored, in digitized form, as a computer file. Preferably, a standardized fixation, staining and electronic image recording procedure is adopted to minimize variations in such procedures, and to enhance the reliability of derived data. Examples are specifications for the fixed setting of the aperture stop in microphotometry, and specifications for the ratio of sampling at the face of the video-detector and the point spread function of an objective.

The stored electronic image is represented as an array of digital values representing the gray-scale values, or "image optical density" (O.D.), at each image point, or picture element (pixel). The gray-scale value at each pixel represents the amount of light absorbing material at each corresponding location in the object, i.e. the histopathologic section. The microscopic structures in the clinical biopsy may be grouped into tissue-architectural components, and nuclear characteristics. The former are assessed by histometric methods, and the latter by karyometric measures. Both may be used to assess the state of a lesion in numeric terms.

Of particular utility for an assessment of the state of a lesion is the nuclear chromatin, i.e., the stained granules found within the boundary of the cell nuclei. The chromatin consists of the genomic material and co-occurring nucleoproteins. The stained granules are formed during fixation to preserve the biopsy material. However, the fonnation of such stained granules, while an artefact, is by no means a random process; rather, it reflects in its spatial and statistical distribution of the nuclear granular chromatin the presence of condensed and non-condensed chromatin in the interphase nucleus. The chromatin distributional characteristics are highly reproducible and indicative of the functional state of the cell nucleus at the time of fixation. The characteristics of the chromatin distribution of the nuclei are highly sensitive and change relatively quickly in response to changes in the in the physiological state of the cell. The study of sectioned images of such cell nuclei is sometimes referred to as nuclear morphometry.

The spatial and statistical distribution of the nuclear chromatin can be measured in numeric form in a number of ways. Each such measure is called a "chromatin texture feature", or simply a "feature". For example, summarizing measures or averaging measures include the sum of all pixel gray-scale values within a nuclear boundary, the average pixel optical density in a nucleus, and the standard deviation of pixel optical density values in a nucleus. Statistical measures can also be used, such as the relative frequency of occurrence of gray-scale values in the intervals of a histogram spanning the range of optical density values. There are measures of the frequency of occurrence of differences between gray-scale values at adjacent pixel locations. There are measures of the relative frequency of occurrence of pairs of gray-scale values at adjacent pixels wherein the gray-scale values at the two adjacent pixels fall into different gray-scale value ranges. Another measure that can be used is the relative frequency of "runs", i.e., of continuous sequences of pixels all falling into the same gray-scale value interval, along a scan line in the digitized image. There are also various measures of "clumping" of the nuclear chromatin, and of the tendency of such nuclear chromatin to be massed at the nuclear periphery.

To derive a measure of lesion progression or regression, based on an assessment of chromatin texture features, the following steps are necessary. First, a calibrated digitized image of the microscopic preparation of a biopsy is recorded, in the general manner described above using the microphotometer and frame-grabber board of the computer. The image is "segmented", i.e., processed by standard image processing procedures to outline the different histologic components and nuclei and to store them separately. Following such segmentation, one or more different measures of chromatin texture features are computed for each nucleus in the digitized image; the actual number of such measures of chromatin texture features that are computed could be as many as 100. This is done for representative biopsy material from normal tissue and from tissue from histopathologically identified cases representing different grades of lesion progression, up to cases with progression to malignant disease.

After gathering the data described above for different grades of lesion progression, standard statistical measures are employed to characterize these data sets for each grade of lesion progression, e.g., mean values, correlations, and standard deviations. Then, a feature selection procedure is applied to reduce the number of measured chromatin texture features to a smaller number, selecting only those features which undergo a monotonic change as the tissue changes from normal tissue to a malignant lesion. These features are selected such that the difference in values between normal tissue and malignant tissue is statistically significant.

Next, standard multivariate methods are applied to derive a linear combination of the best discriminating features, i.e., to weight each of the selected subset of chromatin texture features such that the numeric value of their linear combination leads to a useful method for distinguishing nuclei of normal tissue from nuclei of malignant tissue. The numeric value of such a linear combination of discriminating features is also referred to as the "discriminant function score", and such a score can be computed for each individual nucleus, or averaged for a set of such nuclei, within a particular grade of lesion development. This is done for the data sets representing the different grades of lesion progression, and the mean values are connected by a trend line, or progression curve. An error analysis procedure is employed to determine the interval of uncertainty along the progression curve that determination of progression for a given nucleus, or a given lesion involves. This is the basis for assessment of whether a statistically significant change in progression or regression has occurred in a lesion assessed prior to, and following, chemopreventive or therapeutic intervention.

After the foregoing procedure has been performed for lesions of known grades, samples from unknown lesions can then be assessed. For an unknown lesion, measurement of the features included in the discriminant function, and computation of the discriminant function score, for the lesion allow a projection onto the previously-established progression curve. Progression or regression is then assessed on the basis of two consecutive biopsies separated by given interval of time, noting the change in location along the progression curve in conjunction with an evaluation of the statistical significance of such a change.

One may define a given point on the progression curve as critical point and use it as a surrogate endpoint biomarker (SEBM) in chemoprevention. Alternatively, one may use the process of regression, persistence or even further progression as such marker. A distinctive advantage of using histometric and, in particular, karyometric features as SEBM's for a numeric assessment of efficacy of chemopreventive or therapeutic agents is that these phenotypic criteria are continuous in their value, and that they are reversible, as contrasted to SEBM's based on the detection of molecular genetic defects which are not reversible. Thus, a chemopreventive agent may well be highly effective in halting progression of a lesion and in causing regression, yet the original molecular defect would still be detected, suggesting no chemopreventive efficacy.

One of the advantages of using the present invention is that karyometric features and their changes can be detected long before visual microscopic examination could detect any lesion, i.e., efficacy of chemopreventive intervention can now be established at early stages of lesion development when chemopreventive intervention is most likely to succeed. Moreover, the numeric documentation of chemopreventive efficacy enabled by the invention allows much shorter duration in clinical trials, and effective testing of a much larger number of potentially effective agents. In addition, because the present invention uses karyometric procedures rather than more general histometric procedures, the present invention responds more quickly to changes in the tissue, requires less tissue for the assessment, and is less subject to sampling vagaries.

As indicated above, one application of the present invention is to analyze severely sun damaged skin, and to quantify the progression of solar keratotic skin lesions to squamous cell cancers. In one such study, applicants sought to determine whether the present invention could be used in a practical manner to allow objective grading of such lesions, and to measure progression of skin damage, as well as regression following treatment. In conducting such study, imagery from sections of skin shave biopsies from 12 individuals of fair skin type were digitized. A minimum of 25 nuclei from a solar keratotic lesion and 25 nuclei from a location in histologically normal appearing skin adjacent to the lesion were recorded for each case. Values of karyometric features were computed and a discriminant function distinguishing normal nuclei from nuclei exhibiting solar irradiation damage was derived. The results of such study showed that approximately 50% of nuclei in solar keratotic lesions were found to be markedly affected by solar irradiation, but even in biopsies from histologically normal appearing skin from 3–30 percent of nuclei show signs of such damage. Nuclei from solar keratotic lesions exhibiting such damage have numerous morphometric and karyometric features commonly found in malignant cells. The state of progression of a solar keratotic lesion can be graded by a plot of proportion of nuclei exhibiting solar damage versus the average discriminant function score of the most affected nuclei. This plot provides a monotonically rising progression curve and a numeric grading score. Applicants concluded, based upon such study, that karyometry of nuclei from skin biopsies using the present invention allows an objective assessment of the progression of solar keratotic lesions; that there is a similarity of feature values in nuclei from solar keratotic lesions to those found in malignant lesions; and that the progression curve derived in this study could serve to measure the efficacy of chemopreventive or therapeutic intervention.

In this pilot study, only a limited number of cases were included, all of the same, fair skin type. Skin biopsies from twelve individuals were available. In each case, measurements were taken from a 4 mm. skin shave biopsy within the regions visually identified as solar keratosis and a second set of skin shave biopsy measurements was taken from a region adjacent to those lesions, but clinically normal appearing. Skin shave biopsies were fixed in ethanol and then sectioned to 5 micron thickness and stained with H&E, all slides being stained in the same staining bath.

Low power photomicrographs were taken and the regions of solar keratosis and of adjacent, normal appearing skin delineated. The nuclei chosen for measurement were selected by an experienced dernato-pathologist. The selection criteria were that the nuclei had a diagnostically typical or relevant cytology or pattern, and did not exhibit noticeable distorting sectioning artifacts. While this inevitably introduces some bias, the procedure tends to relate a quantitative characterization to current practice in visual diagnostic assessment.

Measurements were taken on a video-photometer equipped with a Zeiss planapochromatic objective 63:1, N.A. 1.4. The image projection onto the face plate of the vidicon provided a sampling density of six pixels per micron. A narrow band interference filter with maximum transmission at 620 nm was used to enhance contrast. For skin shave biopsies obtained from each patient from both solar keratosis and clinically normal appearing regions, an average of 25 nuclei were measured, segmented and analyzed. Thus, a total of 600 nuclei were measured. For each of the images, the values of a set of nuclear features were computed, including morphometric features and features descriptive of nuclear chromatin texture and spatial distribution.

The data set representing nuclei from solar keratosis shows that, on the average, nuclei are of larger size, stain to considerably higher density, and have a higher variability in the optical density of the stained chromatin granules. Table I below provides a comparison for morphometric feature values averaged over the 300 nuclei each from normal, and solar keratosis regions. All feature values are given in relative units.

TABLE I

Values of nuclear morphometric features in relative units

| | "normal" region | solar keratosis region |
|---|---|---|
| Nuclear area | 33.3 | 54.37 |
| Total optical density | 0.3616 | 0.8762 |
| RMS chromatin | 24.99 | 39.82 |
| Average optical density | 1.118 | 1.61 |

Figure 2:
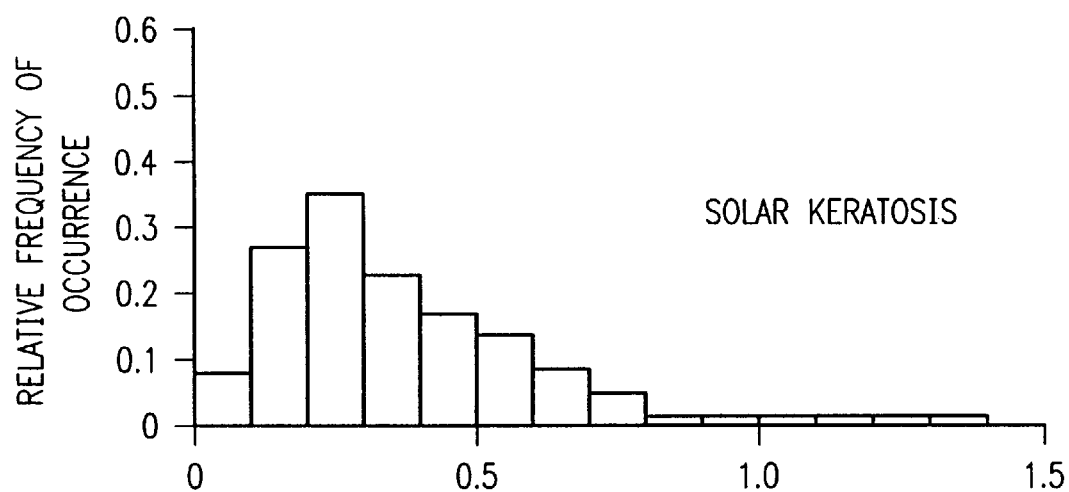
Figure 3:
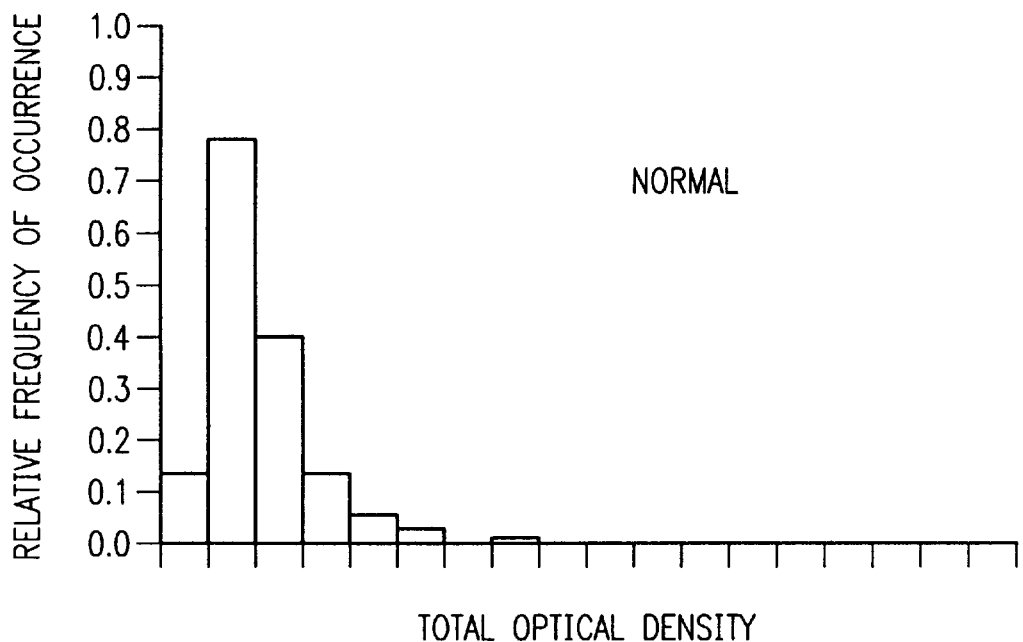
FIGS. 3 and 4 are graphs showing the relative frequency of occurrence of particular total optical densities of nuclei sampled from normal tissue and from solar keratosis lesions, respectively.
Figure 4:
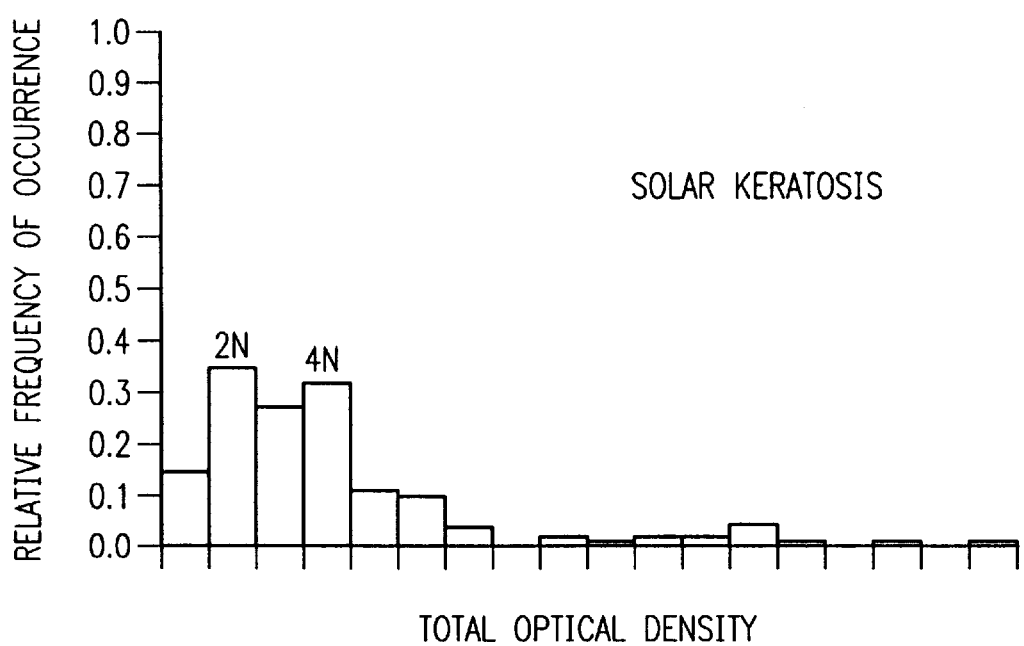

In the above table, the term "RMS", or root mean square, refers to the standard deviation of pixel optical densities in the nucleus. FIGS. 1 and 2 are pixel optical density histograms for normal tissue and solar keratosis lesion tissue, respectively. FIGS. 1 and 2 demonstrate that the histogram for nuclei from the solar keratosis lesion shows an extension into the high optical density range compared with the histogram for normal tissue. FIGS. 3 and 4 show the distribution of total optical density values for the normal tissue data set and the solar keratosis data set, respectively. Nuclei from solar keratosis lesions follow a distribution far into the range of very high values, with an indication of a bimodal distribution. While H&E staining is not stoechiometric for DNA contents, the distribution of total optical density values closely correlates with ploidy distribution. FIG. 4 shows that this set of nuclei contains a substantial proportion of nuclei with ploidy values in excess of 5N.

The problem faced in the analysis and interpretation of these data is the inhomogeneity of the prototypes "histologically normal", and "solar keratosis lesion". To identify the changes induced by solar radiation, observable in individual cells, it is therefore necessary to explore the structure of both data sets and to attempt to identify those cells which exhibit ultra-violet radiation induced changes. In a first attempt at the identification of features expressing solar radiation induced changes, the entire set of feature values was submitted to a Kruskal Wallis test. This test pointed to a substantial number of features with statistically significant changes between the two different sets of biopsies. Morphometric features from several different groups, such as features descriptive of nuclear chromatin texture, runlength statistics, frequency of occurrence of pixel optical density values in certain histogram bins (i.e., first order statistics of the chromatin texture), and features defining nuclear area, average staining density and total optical density were confirmed as having discrimination potential.

Since values of different morphometric features within each of these feature groups tend to be fairly highly correlated, the best features from each feature group were selected and entered into a discriminant analysis. This resulted in a statistically highly significant separation for the two sets of biopsies. Table II below shows the classification matrix for the nuclei.

TABLE II

| | Classification decision | |
|---|---|---|
| True origin | normal | solar keratosis |
| Histologically normal | 79.5% | 20.5% |
| solar keratosis | 45.6% | 54.4% |

On the average, roughly 50% of nuclei from solar keratosis exhibit morphometric feature values significantly different from those found in apparently normal skin. However, about 20% of the nuclei measured in clinically normal appearing skin regions show at least some such effects. The above results represent values averaged over different cases and different lesions. The distribution of discriminant function scores among the different patients shows that there is considerable patient-to-patient variability in these proportions, as seen in Table III presented below:

TABLE III

| | % affected nuclei | | Avg. discrim. function score | |
|---|---|---|---|---|
| Case # | Histologically normal | Solar keratosis lesion | Histologically normal | Solar keratosis lesion |
| 1 | 17% | 96% | −0.368 | +2.001 |
| 2 | 3 | 41 | −0.800 | +0.190 |
| 3 | 12 | 33 | −0.360 | −0.197 |
| 4 | 36 | 85 | −0.350 | +1.025 |
| 5 | 0 | 42 | −0.526 | +0.079 |
| 6 | 11 | 69 | −0.365 | +0.531 |
| 7 | 6 | 65 | −0.313 | +0.402 |
| 8 | 13 | 40 | −0.534 | +0.059 |
| 9 | 73 | 87 | +0.443 | +1.563 |
| 10 | 58 | 67 | +0.211 | +0.108 |
| 11 | 3 | 4 | −0.749 | −0.658 |
| 12 | 3 | 18 | −0.689 | −0.584 |

Figure 5:
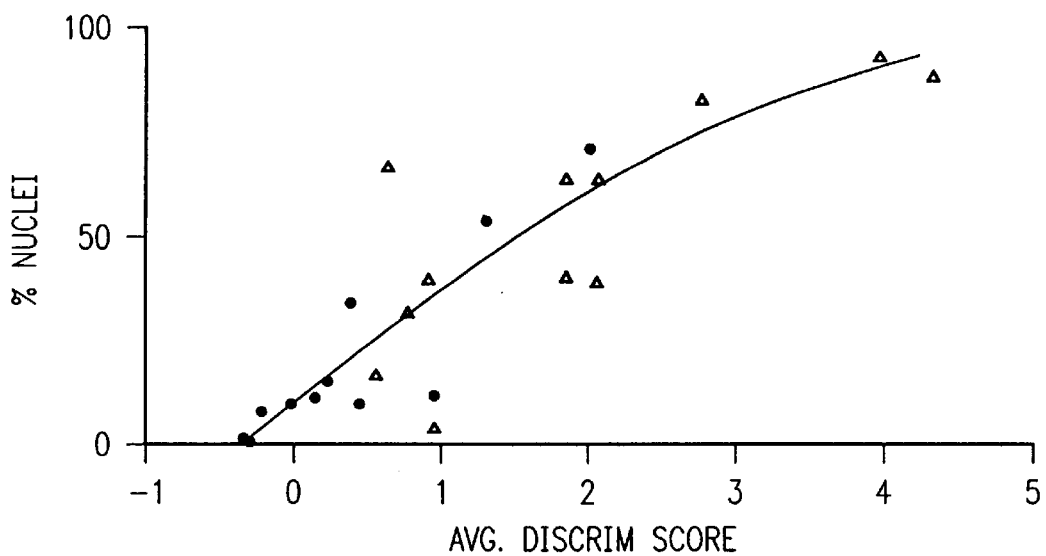
FIG. 5 is a monotonically increasing progression curve serving to index the progression of a solar keratosis lesion.

One can use the data from this study to construct a nuclear grading index for the progression of solar keratosis lesions. From each sampled area, the discriminant function scores for the three most affected nuclei are averaged, to provide a measure of solar radiation effect. These values are plotted along the abscissa. On the ordinate, one plots the proportion of affected nuclei. The result is a monotonically rising curve which can serve as an index for the progression of a solar keratosis lesion. FIG. 5 shows such a progression curve.

Biopsies from normal appearing skin, in most cases (10 out of 12) show a great majority of nuclei classified as "normal" (negative average discriminant function score) and only a modest proportion of nuclei exhibit characteristics of solar keratotic damage. There were two cases though where even in the normal appearing tissue—i.e., clearly outside of any solar keratotic lesion—the majority of nuclei show feature values suggestive of solar keratotic damage, as seen by the positive average discriminant function score. Overall, among the nuclei from normal appearing tissue, 20% show ultra-violet radiation damage effects; if the two cases with the much higher proportions of affected cells are treated as outliers, this proportion would reduce, on the average, to about 10%.

The selection and weighting of variables indicative of the degree of change due to solar keratosis is affected, in the above discriminant function analysis, by the admixture of nuclei exhibiting such change in the set of "normal" nuclei, and the admixture of nuclei exhibiting only minimal effects in the set of nuclei from solar keratosis. The expectation is that one might observe at least some bimodality in the distribution of discriminant function scores. One might then select subpopulations with extreme discriminant function scores to form training sets less affected by inhomogeneities, and be able to identify a possibly more effective linear combination of features to characterize affected cells. When this is done, an only slightly different set of features is selected. However, the covariance structure in the original feature set was almost the same for "normal" and for "affected" nuclei; the same similarity in covariance structure is found for the two more homogeneous subpopulations used in this second analysis. Consequently, no significant improvement in discrimination or change in observed proportions of cells affected by solar irradiation is observed.

The study described above shows that it is possible to measure the grade of a solar keratosis lesion based on the proportion of affected nuclei, and the average discriminant function score for the most affected nuclei in a biopsy sample. The study suggests that one must measure a sample of nuclei of a size adequate to provide an accurate estimate of the proportion of affected nuclei. It is fortunate that the similarity of covariance of morphometric feature values in the clinically normal appearing and solar keratosis lesion samples was such that the inhomogeneity of the nuclear samples (due to the presence of clearly affected or minimally affected nuclei respectively in both samples) did not prevent the identification of characterizing features.

The above described procedure lends itself for the measurement of degree and rate of progression of solar keratosis lesions. It was unexpected to find a substantial proportion of affected nuclei in the visually normal appearing tissue adjacent to the solar keratosis lesions. The nuclei expressing solar damage effects exhibit a pattern of morphometric feature values, or a "signature", which image analysis of nuclei from other body sites has regularly associated with malignant transformation. The affected nuclei found in this study have many of the characteristics of malignant cells, an observation that raises concerns about the management of these lesions, and possibly the need for the identification of individuals at high risk to develop invasive squamous cell cancers.

Figure 6:
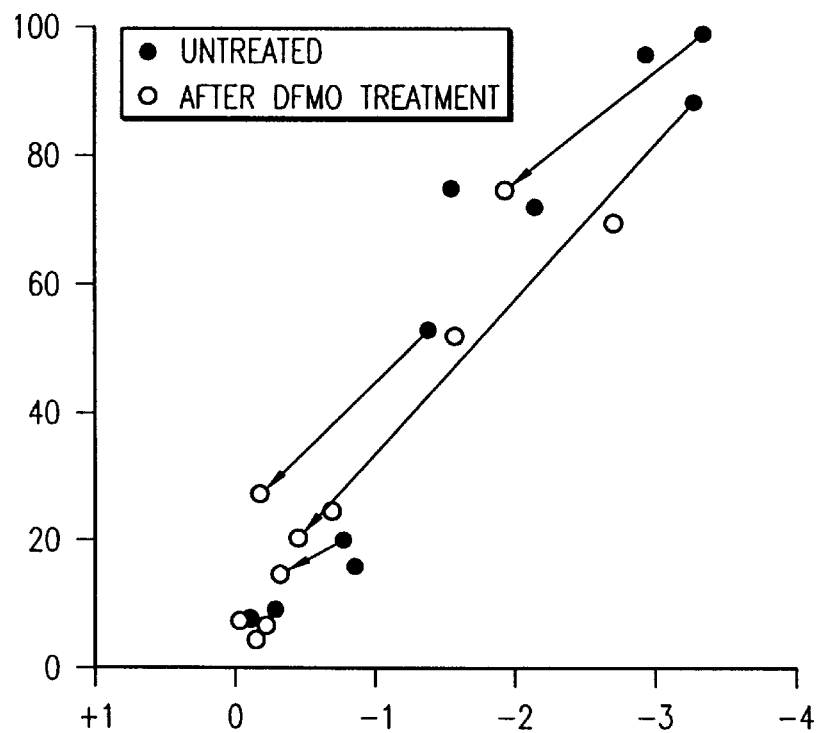
FIG. 6 is a graph illustrating the efficacy of the use of DFMO to treat solar keratosis lesions.

Likewise, the procedure of the present invention is useful in measuring the efficacy of a chemopreventive intervention. The above derived progression curve and the associated discriminant function were then employed in a feasibility study on the efficacy of DFMO in treating solar keratosis lesions. It can be shown, in repeat biopsies, that the majority of cases exhibit a regression—downwards along the progression curve—with respect to both the averaged discriminant function scores, and the proportion of affected nuclei. This is shown in FIG. 6.

Figure 7:
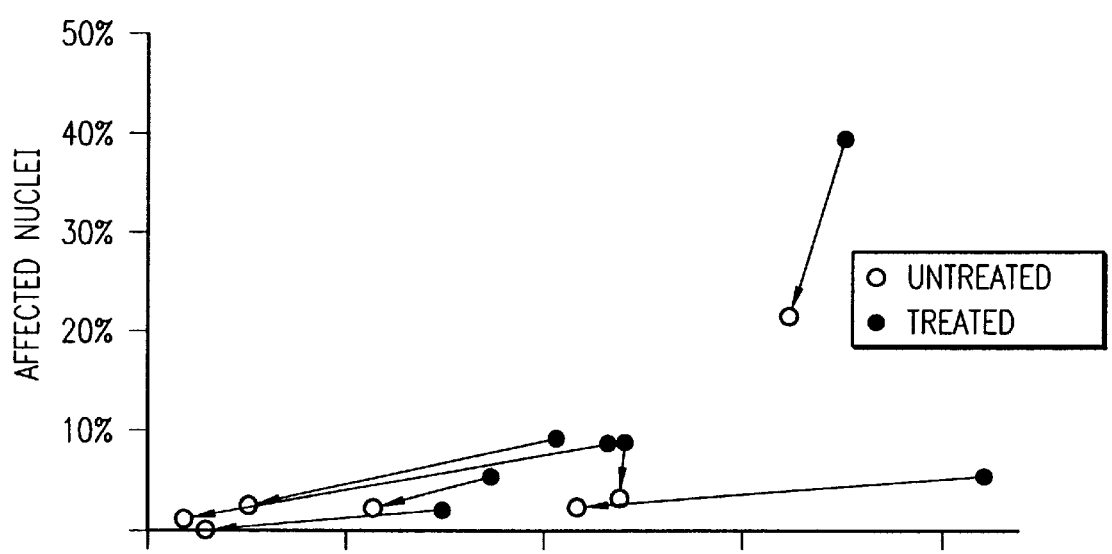
FIG. 7 is a graph illustrating the efficacy of the use of Vitamin A to treat solar keratosis lesions.

Similar results were obtained from a feasibility study of the efficacy of Vitamin A in the prevention of skin lesions. The biopsies submitted here did not come from solar keratotic lesions, but from exposed skin that histopathologically had been adjudged as "normal". Measurement shows that this seemingly undamaged tissue does contain damaged cell nuclei. Even though the proportion of affected nuclei is rather small, only a few percent, the extent of damage in these nuclei, as assessed by the discriminant function scores is severe. Vitamin A treatment resulted in a reduction of the proportion of damaged nuclei in every one of these cases, and in the extent of damage measured in these nuclei. This is shown in FIG. 7.

While the above studies related to solar keratosis skin lesions, similar studies have been performed using the present invention relative to prostatic lesions, with promising results. For example, see Bartels, et al., "Nuclear Chromatin Texture in Prostatic Lesions", *Analytical and Quan-* titative *Cytology and Histology*, Vol. 20, No. 5, October 1998, pp. 389–406, the disclosure of which publication are hereby incorporated by reference as if fully set forth herein.

Those skilled in the art will now appreciate that a method has been described for quantitatively measuring the progression of a lesion along a progression curve ranging between normal tissue and malignant disease. The described method allows a user to objectively assess and grade sampled tissue to assign a progression index value to a lesion, and further allows a user to quantitatively detect and assess changes in tissue over a relatively short period of time. As indicated above, the described method further allows one to rapidly and quantitatively determine the efficacy of a chemopreventive drug or treatment in combating progression of tissue from its normal state toward malignant disease.

While the present invention has been described with respect to preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

We claim:

1. A method for quantitatively measuring the progression of a lesion, said method comprising the steps of:
   a. preparing a clinical sampled section of a current biopsied lesion;
   b. magnifying the sampled section of the current biopsied lesion;
   c. forming a video image of the magnified sampled section with a video camera;
   d. digitizing the video image formed by the video camera;
   e. storing the digitized video image electronically;
   f. analyzing the stored digitized video image to locate a plurality of cell nuclei within said digitized video image;
   g. computing at least one chromatin texture feature of a predetermined type of each of said plurality of cell nuclei; and
   h. comparing the at least one computed chromatin texture feature of the plurality of nuclei from the current biopsied lesion to a range of previously computed chromatin texture features of the same predetermined type for lesions that range along a progression curve from normal tissue to malignant disease, in order to measure the degree to which the current lesion has progressed from normal tissue toward malignant disease.

2. The method recited by claim 1 wherein steps a. through h. are repeated after a predetermined time has elapsed to detect whether the lesion is progressing toward malignant disease or regressing away from malignant disease.

3. The method recited by claim 2 wherein movement of the at least one computed chromatin texture feature along the progression curve during said predetermined time is used to measure the efficacy of a method for treating such lesion.

4. The method recited by claim 2 wherein chemopreventive intervention is practiced upon a patient having such lesion, and wherein said method is used to determine whether, and by how much, such chemopreventive intervention is causing such lesion to regress away from malignant disease.

5. The method recited by claim 2 wherein therapeutic intervention is practiced upon a patient having such lesion, and wherein said method is used to determine whether, and by how much, such therapeutic intervention is causing such lesion to regress away from malignant disease.

6. The method recited by claim 1 wherein said at least one chromatin texture feature is one which undergoes a monotonic change from normal tissue to a malignant lesion.

7. The method recited by claim 6 wherein said at least one chromatin texture feature is one which undergoes a statistically significant change as between normal tissue and malignant disease.

8. The method recited by claim 1 wherein the lesion is a skin tissue lesion.

9. The method recited by claim 1 wherein the lesion is a prostatic lesion.

10. The method recited by claim 1 wherein the lesion is a breast tissue lesion.

11. The method recited by claim 1 wherein the lesion is endometrial tissue.

12. The method recited by claim 1 wherein the lesion is esophogeal tissue.

13. The method recited by claim 1 wherein the at least one computed chromatin texture feature is the total optical density for said plurality of cell nuclei.

14. The method recited by claim 1 wherein said step of magnifying the sampled section of the current biopsied lesion, and forming a video image thereof are performed using a microphotometer.

15. A method for quantitatively measuring the efficacy of chemopreventive gents, said method comprising the steps of:
   a. preparing a clinical sampled section of current biopsied tissue from a patient;
   b. magnifying the sampled section of the current biopsied tissue;
   c. forming a video image of the magnified sampled section with a video camera;
   d. digitizing the video image formed by the video camera;
   e. storing the digitized video image electronically;
   f. analyzing the stored digitized video image to locate a plurality of cell nuclei within said digitized video image;
   g. computing at least one chromatin texture feature of a predetermined type of each of said plurality of cell nuclei;
   h. comparing the at least one computed chromatin texture feature of the plurality of nuclei from the current biopsied tissue to a range of previously computed chromatin texture features of the same predetermined type for biopsied tissue that ranges along a progression curve from normal tissue to malignant disease, in order to measure the degree to which the current biopsied tissue has progressed from normal tissue toward malignant disease;
   i. applying a chemopreventive agent to the patient;
   j. waiting a predetermined amount of time for the chemopreventive agent to have an effect; and
   k. repeating steps a. through h. above relative to another current biopsied tissue from such patient to determine whether, and how much, the biopsied tissue has regressed away from malignant disease, and hence, the effectiveness of the chemopreventive agent.

16. The method recited by claim 15 wherein said at least one chromatin texture feature is one which undergoes a monotonic change from normal tissue to a malignant lesion.

17. The method recited by claim 16 wherein said at least one chromatin texture feature is one which undergoes a statistically significant change as between normal tissue and malignant disease.

18. The method recited by claim 15 wherein the biopsied tissue is skin tissue.

19. The method recited by claim 15 wherein the biopsied tissue is prostate tissue.

20. The method recited by claim 15 wherein the biopsied tissue is breast tissue.

21. The method recited by claim 15 wherein the biopsied tissue is endometrial tissue.

22. The method recited by claim 15 wherein the biopsied tissue is esophogeal tissue.

23. The method recited by claim 15 wherein the at least one computed chromatin texture feature is the total optical density for said plurality of cell nuclei.

24. The method recited by claim 15 wherein said step of magnifying the sampled section of the current biopsied tissue, and forming a video image thereof are performed using a microphotometer.

* * * * *